United States Patent
Mathieu

(10) Patent No.: US 8,435,964 B2
(45) Date of Patent: May 7, 2013

(54) ECTONUCLEOTIDASE PYROPHOSPHATE/PHOSPHODIESTRASE-1 (ENPP-1) AS A TARGET FOR THE TREATMENT OF AORTIC VALVE STENOSIS AND CARDIOVASCULAR CALCIFICATION

(75) Inventor: Patrick Mathieu, Lac Beauport (CA)

(73) Assignee: Universite Laval, Quebec, Quebec (CA)

( * ) Notice: Subject to any disclaimer, the term of this patent is extended or adjusted under 35 U.S.C. 154(b) by 26 days.

(21) Appl. No.: 12/908,467

(22) Filed: Oct. 20, 2010

(65) Prior Publication Data
US 2011/0098243 A1 Apr. 28, 2011

Related U.S. Application Data

(60) Provisional application No. 61/253,939, filed on Oct. 22, 2009.

(30) Foreign Application Priority Data

Oct. 22, 2009 (CA) ..................................... 2684017

(51) Int. Cl.
*G01N 33/573* (2006.01)
*C12Q 1/44* (2006.01)
*A61K 31/7076* (2006.01)
*C07H 19/20* (2006.01)
*A61P 9/00* (2006.01)

(52) U.S. Cl.
USPC .............. 514/47; 435/19; 435/7.4; 536/26.26

(58) Field of Classification Search .................... 514/47; 435/19, 7.9, 7.4; 536/26.26
See application file for complete search history.

(56) References Cited

PUBLICATIONS

Pepin et al., Circulation: 118 (18 suppl. 2), S1019-S1020 (2Oct. 28, 2008).*
Giachelli C.M. et al., 2001, "Vascular calcification and inorganic phosphate.", Am. J. Kidney Dis., 38: S34-S37.
Rutsch F. et al., 2001, "PC-1 nucleoside triphosphate pyrophosphohydrolase deficiency in idiopathic infantile arterial calcification.", Am. J. Pathol., 158: 543-554.
Masuda I. & Hirose J., 2002, "Animal models of pathologic calcification.", Curr. Opin. Rheumatol., 14: 287-291.
Johnson K. et al., 2001, "Up-regulated expression of the phosphodiesterase nucleotide pyrophosphatase family member PC-1 is a marker and pathogenic factor for knee meniscal cartilage matrix calcification.", Arthritis Rheum., 44: 1071-1081.
Levesque S.A. et al., 2007, "Specificity of the extoATPase inhibitor ARL 67156 on human and mouse ectonucleotidases.", Br. J. Pharmacol., 152: 141-150.
Thouverey C. et al., 2009, "Inorganic Pyrophosphate as a regulator of hydroxyapatite or calcium pyrophosphate dihydrate mineral deposition by matrix vesicles.", Osteoarthritis, Cartilage, 17: 64-72.
Crack B.E. et al., 1995, "Pharmacological and Biological analysis of FPL67156, a novel, selective inhibitor of ectoATPase.", British Journal of Pharmacology, 144: 475-481.
Hessle L. et al., 2002, "Tissue-nonspecific alkaline phosphatase and plasma cell membrane glycoprotein-1 are central antagonistic regulators of bone mineralization.", PNAS, 99(14): 9445-9449.
Harmey D. et al., 2004, "Concerted Regulation of Inorganic Pyrophosphate and Osteopontin by Akp2, Enpp1, and Ank: An Integrated Model of the Pathogenesis of Mineralization Disorders.", American Journal of Pathology 164(4): 1199-1209.
Bossé Y., 2008, "The Next Step to Elucidate the Etiology of Calcific Aortic Valve Stenosis.", Journal of American College of Cardiology, 51(14): 1327-1336.
Narisawa S. et al., 2007, "Novel Inhibitors of Alkaline Phosphatase Suppress Vascular Smooth Muscle Cell Calcification.", Journal of Bone and Mineral Research, 22(11): 1700-1710.
Giachelli C.M., 2009, "The emerging role of phosphate in vascular calcification.", Kidney International, 75: 890-897.
Li X. And Giachelli C.M., "Sodium-dependent phosphate cotransporters and vascular calcification.", Current Opinion in Nephrology and Hypertension, 16: 325-328, (2007).
Li X. et al., 2006, "Role of the Sodium-Dependent Phosphate Cotransporter, Pit-1, in Vascular Smooth Muscle Cell Calcification.", Circulation Research, Published by the American Heart Association, Dowloaded from www.circes.ahajournals.org, on Jul. 15, 2009.

* cited by examiner

*Primary Examiner* — Chih-Min Kam
(74) *Attorney, Agent, or Firm* — Norton Rose Canada LLP

(57) ABSTRACT

Aortic valve stenosis (AS) is a chronic process related to a progressive mineralization of the aortic root and valve cusps. We found in human AS valves a high level of expression and enzymatic activity of ectonucleotide pyrophosphatase/phosphodiesterase-1 (ENPP-1), which correlated to the degree of mineralization. In vitro, inhibition of ENPP activity with ARL 67156 significantly reduced calcification of isolated valve interstitial cells. In a rat model of cardiovascular calcification, ARL 67156 significantly reduced calcification of the aortic root and valve cusps. This is the first study to demonstrate that increased expression and activity of ENPP-1 promotes the mineralization process in AS valves. Hence, inhibition of ectonucleotidase may represent a novel target of therapy for this frequent and serious cardiovascular disease.

7 Claims, 5 Drawing Sheets

ECTONUCLEOTIDASE PYROPHOSPHATE/PHOSPHODIESTRASE-1 (ENPP-1) AS A TARGET FOR THE TREATMENT OF AORTIC VALVE STENOSIS AND CARDIOVASCULAR CALCIFICATION

CROSS-RELATED APPLICATIONS

This application claims priority from U.S. provisional application 61/253,939 filed on Oct. 22, 2009 and from CA application 2,684,017 filed on Oct. 22, 2009, both of which are incorporated by reference herein in their entirety.

FIELD OF THE INVENTION

The present invention relates to the treatment and/or prevention of aortic valve stenosis (AVS) and cardiovascular calcifications. Particularly, the invention provides a target for intervention in the treatment or prevention of AVS through ectonucleotide pyrophosphatase/phosphodiesterases (EN-PPs) and an assay for identifying anti-calcifying agents for the treatment of AVS by testing potential inhibitors of ENPP-1. More particularly, the invention provides means to treat and/or prevent AVS by reversing or slowing the calcification process by administering an inhibitor of ENPP-1. Also, the invention provides means to treat hypertension related to decreased arterial compliance and vascular calcification.

BACKGROUND OF THE INVENTION

Calcific aortic valve stenosis (AVS) is the most frequent heart valve disorder. The culprit disease process of AVS is the progressive mineralization of the aortic valve, including the aortic valve cusps, annulus, and root. The incidence of this disease increases with age, hypertension, diabetes, dyslipidemia, and is often associated with a bicuspid aortic valve, a congenital abnormality present in 1-2% of the population. AVS is a slow and progressive disorder that can be diagnosed at an early stage with the use of cardiac auscultation and Doppler-echocardiography. This disease pattern thus provides a relatively long time window of opportunity, during which patients might be treated by pharmacologic agents before mineralization of the valve becomes too extensive and causes a severe obstruction to left ventricular outflow tract. Unfortunately, there is currently no medical treatment available to prevent the development and progression of this disease and aortic valve replacement surgery remains the only efficient treatment when AVS becomes severe.

Calcification of the aortic valve is an intricate process involving a balance between promoting and anti-calcifying mechanisms. In this regard, expression of ectonucleotidase enzymes may modulate calcification of the aortic valve. Among those enzymes, ectonucleotide pyrophosphatase/phosphodiesterases (ENPPs), ectonucleoside triphosphate diphosphohydrolases (ENTPDs), and 5'-nucleotidase (NT5E) use nucleotides as substrate and may modulate mineralization. The presence and regulation of these enzymes has never been studied in aortic stenotic (AS) valves.

SUMMARY OF THE INVENTION

The invention provides, for the first time, that ENPP-1 is highly expressed in AS valves and is furthermore a key regulator of the calcifying process. The markedly elevated level of ENPP-1 expression in bicuspid valves may explain the early onset of mineralization and the high magnitude of calcification of valvular tissues observed in patients with this congenital abnormality.

Particularly, the invention provides, means to prevent aortic valve stenosis and vascular calcification by means of regulation (inhibition) of the enzymatic activity of ENPP 1 and ectonucleotidases.

The present invention therefore provides a method for identifying an inhibitor of aortic valve stenosis or vascular calcification, comprising the steps of: a) contacting ectonucleotidase pyrophosphate/phosphodiesterase-1 (ENPP-1) with a potential inhibitor compound thereof; and b) measuring the level of ENPP-1 activity; whereby a lowered activity of ENPP-1 is an indication that said compound may be a potential inhibitor of aortic valve stenosis or vascular calcification.

The invention further provides a method for treating aortic valve stenosis or cardiovascular calcification in a mammal, including human, suffering therefrom, comprising the step of administering a pharmaceutically effective amount of compound inhibiting ectonucleotidase pyrophosphate/phosphodiesterase-1 (ENPP-1: aka PC-1 or EC 3.1.4.1)).

Alternatively, the invention is directed to the use of a compound inhibiting ectonucleotidase pyrophosphate/phosphodiesterase-1 (ENPP-1) for the manufacture of a medicament for the treatment of aortic valve stenosis or cardiovascular calcification in a mammal, including human.

The invention further provides a compound inhibiting ectonucleotidase pyrophosphate/phosphodiesterase-1 (ENPP-1) for use as a treatment of aortic valve stenosis or cardiovascular calcification in a mammal, including human.

The invention further provides the use of ectonucleotidase pyrophosphate/phosphodiesterase-1 (ENPP-1) as a target in the identification of a compound for the treatment of aortic valve stenosis or cardiovascular calcification in a mammal.

The invention further provides assays for identifying potential inhibitors of ENPP-1 that may be useful for the treatment of aortic valve stenosis or cardiovascular calcification in a mammal. Particularly, these assays may take the form of displacement or competition assays with a compound known to bind ENPP-1 and inhibit its enzymatic activity, previously labelled in order to make it easily detectable.

The invention further provides an assay for identifying an inhibitor of ectonucleotidase pyrophosphate/phosphodiesterase-1 (ENPP-1), comprising the steps of:

a) contacting (ENPP-1) with labeled known inhibitor of ENPP-1 to form a ENPP-1+inhibitor complex;

b) contacting the ENPP-1+inhibitor complex with a potential inhibitor compound of ENPP-1;

c) measuring displacement of labeled inhibitor from the complex;

whereby a displaced labeled inhibitor is an indication that said compound may be a potential inhibitor of ENPP-1.

The invention further provides an assay for identifying an inhibitor of ectonucleotidase pyrophosphate/phosphodiesterase-1 (ENPP-1), comprising the steps of:

a) contacting a labeled ARL-67156:

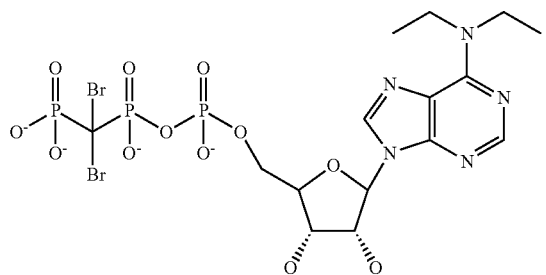 [SMILES: CCN(CC)c1ncnc2c1ncn2C1OC(COP(=O)([O-])OP(=O)([O-])C(Br)(Br)P(=O)([O-])[O-])[C@@H](O)[C@H]1O]

with a potential inhibitor compound of ENPP-1 to form a ARL-67156+inhibitor mixture:
b) contacting the ARL-67156+inhibitor mixture with ENPP-1;
c) measuring the amount of labeled ARL-67156 bound to ENPP-1; and
d) comparing to amount of labeled ARL-67156 bound to ENPP-1 in the absence of the potential inhibitor compound;

wherein a lowered amount of labeled ARL-67156 in step c) compared to step d) is an indication that said compound may be a potential inhibitor of ENPP-1 activity.

DETAILED DESCRIPTION OF THE INVENTION

DETAILED DESCRIPTION OF PARTICULAR EMBODIMENTS

Figure 1:
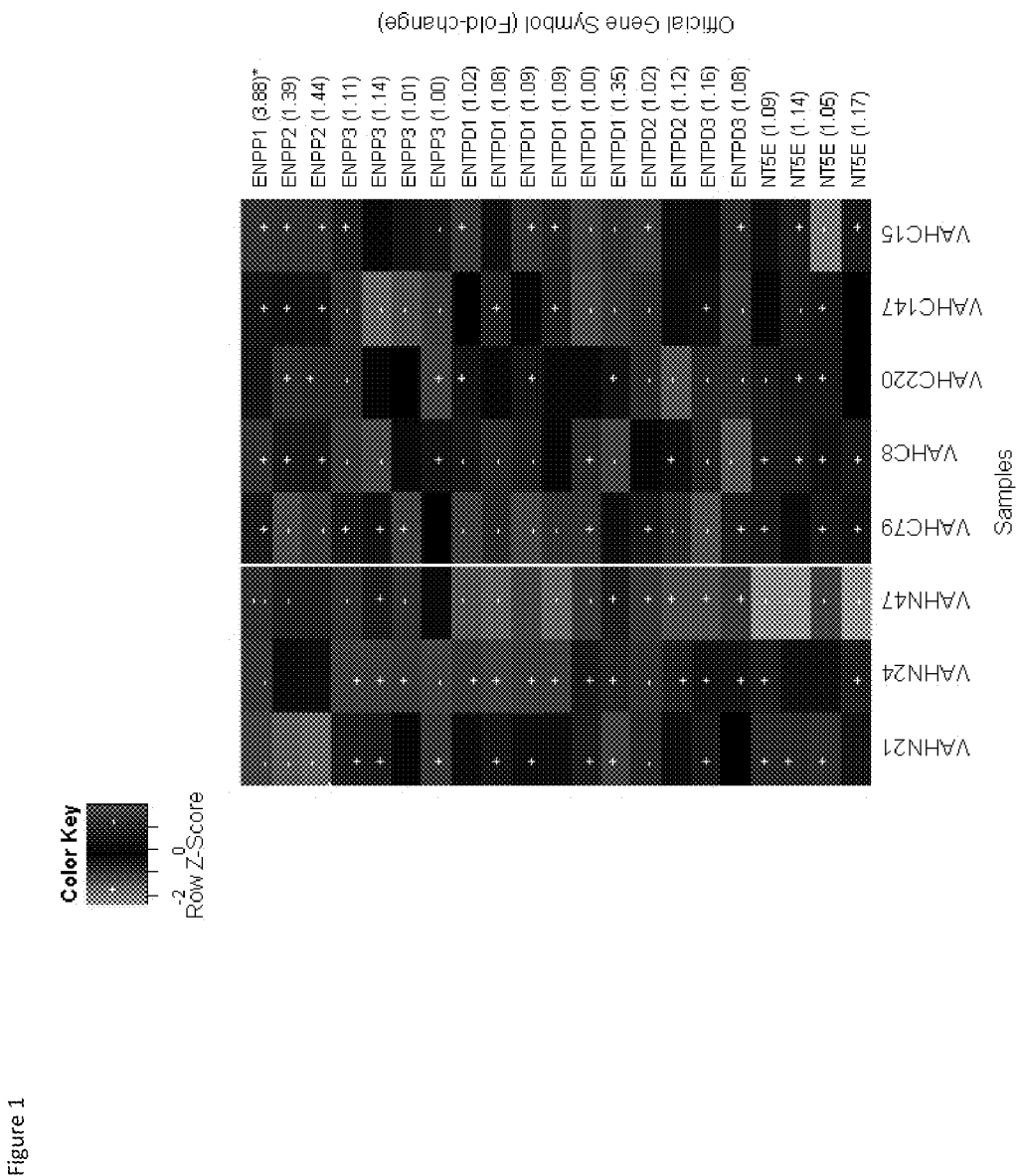
FIG. 1: Gene expression profiles of ectonucleotide pyrophosphatase/phosphodiesterase and ectonucleoside triphosphate diphosphohydrolase families. Transcripts that are up-regulated and down-regulated are shown in grey bearing (+) and grey bearing (−), respectively. The heat map is scaled at the row level to compare expression profile between samples for a given probe sets. The columns represent the aortic valve samples with (VAHC79, VAHC8, VAHC220, VAHC147, VAHC15) and without (VAHN21, VAHN24, VAHN47) AS. Each row represents a different probe set tagging a specific enzyme indicated at the right. The fold-change comparing the expression of stenotic versus control aortic valves is indicated in parentheses. The asterisks represent probe sets that are claim-significant based on the whole microarray experiment. ENPP, ectonucleotide pyrophosphatase/phosphodiesterase; ENTPD, ectonucleoside triphosphate diphosphohydrolase; NT5E, 5'-nucleotidase.

Particularly, with respect to the different embodiments of the present invention such as methods and use, the mammal is particularly a human.

Particularly, with respect to the methods, use and compounds of the present invention, the inhibitor compound is particularly a competitive inhibitor of ENPP-1 activity, more particularly the inhibitor compound is an ATP analog. With respect to the method of treatment and use of the invention, most particularly, the inhibitor compound is ARL-67156:

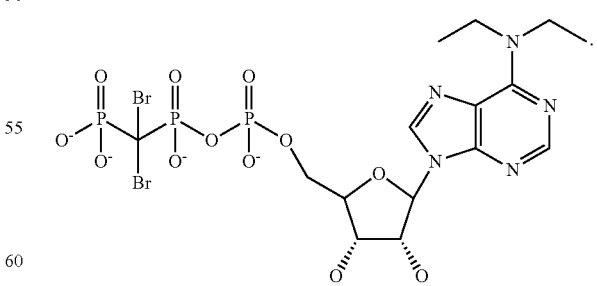

Particularly, with respect to the assay of the present invention, the ARL-67156 may be labelled in such as way as to enable its detection by chemical, or physical methods such as for example spectroscopic, photochemical, biochemical, immunochemical means.

For example, useful labels include fluorescent dyes, electron-dense reagents, enzyme substrates (e.g., as commonly used in an ELISA), biotin, digoxigenin, co-factors, ligands, chemiluminescent agents, radioisotope, fluorophores, colorimetric haptens, enzymatic label, and combinations thereof or other entities which can be made detectable, such that the compound bound to the label or marker can be determined by detecting the labeled marker compound in a complex. For example, compounds (e.g., label substrates) can be labeled with $^{131}I$, $^{125}I$, $^{35}S$, $^{14}C$, or $^{3}H$, either directly or indirectly, and the radioisotope detected by direct counting of radioemission or by scintillation counting. Alternatively, assay components can be enzymatically labeled with, for example, horseradish peroxidase, alkaline phosphatase, beta-galactosidase or luciferase, and the enzymatic label detected by determination of conversion of an appropriate substrate to product. Labels can also be proteins with luminescent properties, e.g., green fluorescent protein and phycoerythrin.

Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Mechanisms Participating to the Regulation of ENNP-1 Expression in Aortic Valve

The expression of ENPPs at the tissue level is widespread and ubiquitous, but current observations indicate that bone cells and fibroblasts express ENPP-1 at a particularly high level. It is suspected that ENPP-1 in bone tissue has a crucial role in regulating the calcifying process. Among different factors, mechanical stress has been demonstrated as a potent external signal promoting the expression of ENPP-1. The findings of the present study also suggest that mechanical stress might be involved in the up-regulation of ENPP-1, since diastolic blood pressure and bicuspid valves were two independent variables associated with higher expression of this enzyme among the AS valves. The mechanical stress imposed on the aortic valve cusps is higher during the diastolic phase of the cardiac cycle. Bicuspid valve configuration is known to create an abnormal blood flow pattern and to increase the mechanical stress on the valve cusps. Patients with bicuspid valves have a higher risk to develop AS during their lifetime. Furthermore, when compared to tricuspid valves, bicuspid stenotic valves explanted at the time of surgery are generally more calcified and remodeled. In light of these findings, we postulated that ENPP activity is increased within congenitally abnormal valves as a result of higher mechanical stress and that this may participate to early and rapid calcification of these valves. Another alternative explanation, although not necessarily exclusive, was that bicuspid valves have intrinsic abnormal regulation pattern of ENPP-1 expression.

ENPP-1 and Calcification of the Aortic Valve

Previous studies have underlined the importance of ENPP-1 as an important regulator of the mineralization process. In fact, one of the main by-products of ENPP-1 activity is PPi, which binds to hydroxyapatite crystals and prevent further development of the mineralization process. (1) This role of ENPP-1 is well illustrated by idiopathic infantile arterial calcification in which a deficiency of ENPP activity is associated with early onset of medial calcification of large arteries. (2) Also, mice deficient for ENPP-1 develop extensive periarticular calcification. (3) Hence, taken together these observations point to the concept that down-regulation of ENPP activity is linked to the mineralization of soft tissue. On the other hand, in knee meniscal cells, the transfection of ENPP-1 promotes the mineralization process and leads to increased production of hydroxyapatite of calcium. (4) Hence, ectopic mineralization of soft tissues is a complex process that involves a delicate balance in ENPP activity. In the present study, we have documented a higher level of ENPP-1 in AS valves when compared to control tissues. Of particular significance, we have also documented a significant and positive correlation between phosphodiesterase activity and valvular concentration of calcium in explanted valves, suggesting that higher activity of ENPP-1 promote calcification of the aortic valve.

In vitro studies, conducted with human valve interstitial cells (VICs), have shown that isolated cells expressed basal levels of ENPP-1, which was increased significantly upon stimulation with the calcifying medium. In fact, addition of $NH_2PO_4$ to the medium induced a dose-dependent increase of ENPP-1 protein and enzymatic activity. Noteworthy, when VICs were cultured with the calcifying medium and ARL 67156 (5), a competitive inhibitor of ENPP-1 activity, calcification was significantly reduced. These observations are thus consistent with the association found at the tissue level between phosphodiesterase activity and levels of calcium in explanted AS valves, and strongly suggest that up-regulation of ENPP-1 in aortic valve promotes the calcifying process.

To further support the role of ENPP-1 in the calcification of the aortic valve we have tested the effect of ARL 67156 in the WVK rat model. In this model, rats under WVK regimen developed extensive mineralization of aortic root and cusps. In these in vivo experiments we found that administration of ARL 67156 at 0.55 μg/kg/day and 1.1 μg/kg/day prevented the development of aortic valve calcifications. Also of particular importance, ENPP-1 was only detected at the proximity of mineralized areas. Taken together, the protective effect of ARL 67156 and the colocalization of ENPP-1 with calcifications, strongly indicates that ENPP activity is involved in the calcification process of the aortic valve in vivo. In this regard, it is also interesting to point out that patients with AVS, and particularly those with bicuspid valves, often have extensive calcification of the aortic root.

EXAMPLES

Example 1

Materials and Methods
Patients and Tissue Collection

We examined 87 aortic valves explanted from patients who underwent aortic valve replacement for calcific AVS. Fourteen aortic valves with normal morphology and function, as documented by Doppler-echocardiography, were obtained from patients undergoing a heart transplantation procedure and used as controls. The protocol was approved by local ethical committee and informed consent was obtained from the subjects. All patients had moderate to severe AVS and less than mild aortic regurgitation. Patients with a history of rheumatic disease, endocarditis or an inflammatory disorder were excluded. Samples were taken at the time of surgery. Two cusps were snap frozen in liquid nitrogen for ulterior quantification of calcium content, protein isolation, and RNA isolation for ulterior quantitative PCR (q-PCR) analyses. One cusp was decalcified in Cal-Ex™ (Fisher, Ottawa, Canada) for 24 hours and then one segment was fixed in formaldehyde 10% for histological processing and the other segment was embedded in optimum cutting temperature (OCT) compound (Somagen diagnostics, Edmonton, Canada) and frozen in liquid nitrogen for immunohistological analysis.

Doppler Echocardiography

All patients underwent a comprehensive Doppler echocardiographic examination before aortic valve replacement surgery. Doppler echocardiographic measurements included the left ventricular stroke volume and transvalvular pressure gradients using modified Bernoulli equation. In a subset of 37 patients in whom two or more serial echocardiograms separated by at least 6 months were available preoperatively, the hemodynamic progression of stenosis was determined Annualized changes in peak gradients (mmHg/year) were calculated by dividing the difference between the first and the last measurements by the time between examinations.

Microarray

A total of five AS valves and five normal aortic valves were selected for microarray application. To reduce heterogeneity, only valves taken from male subjects were selected. The two valve groups were also matched for patient's age and body mass index. Expression studies were performed using the human U133 plus 2.0 Affymetrix GeneChip microarrays (Affymetrix, Santa Clara, Calif., USA). Arrays were processed using a standard Affymetrix double amplification protocol using 80 ng of RNA. Expression values were extracted using the Robust Multichip Average (RMA) method. Quality control assessment was performed with the FlexArray software version RC3 and the Affy package that is part of the Bioconductor project (www.bioconductor.org/). Two microarrays interrogating control valves failed quality control and were discarded from the analysis. Significant Analysis of Microarrays (SAM) method was used to claim significant regulation. The minimum fold change and the delta values was set to 2 and 0.76, respectively, in order to reach a false discovery rate below 5% (4.85%). The microarray dataset can be found in the National Center for Biotechnology Information's Gene Expression Omnibus (GEO) repository (www.ncbi.nlm.nih.gov/geo/) and are accessible through GEO Series accession number GSE12644.

RNA Extraction and Real-Time PCR

In 101 patients (87 AS and 14 controls), RNA was extracted. RNA was also extracted from cells during in vitro experiments. Total RNA was isolated with RNeasy® micro kit from Qiagen (Qiagen, Mississauga, Ont, Canada). The RNA extraction protocol was performed according to manufacturer's instructions using 100 mg of tissue. The quality of total RNA was monitored by capillary electrophoresis (Experion, Biorad, Mississauga, Ont, Canada). Four μg of RNA was reverse transcribed using the Quantitec Reverse Transcription Kit from Qiagen. Quantitative real-time PCR (q-PCR) was performed with Quantitec SYBR Green PCR kit from Qiagen in the Rotor-Gene 6000 system (Corbett Robotics Inc, San Francisco, Calif., USA). ENPP-1 was quantified with real-time q-PCR (coding: TGC CCC TTT GGA CAT CCT ATA CC (SEQ ID NO. 1), non-coding: TTG TGG TGG GGA GAG GAA CC; SEQ ID NO. 2) at the following conditions: an initial 15 min run at 95° C. before starting, then 94° C. for 10 sec, 58° C. for 30 sec, and 72° C. for 30 sec for a total of 40 cycles. The expression of a reference gene, HPRT (coding: TGG CGT CGT GAT TAG TGA TG; SEQ ID NO. 3, non-coding: AAT CCA GCA GGT CAG CAA AG; SEQ ID NO. 4), was chosen as a normalizer to control for any difference in the amount of cDNA starting material. The real-time PCR for HPRT was carried out at the following conditions: an initial 15 min run at 95° C. before starting, then 94° C. for 10 sec, 58° C. for 30 sec, and 72° C. for 30 sec for a total of 40 cycles. Both primers were home designed and synthesized by Invitrogen (Invitrogen, Toronto, Ont, Canada).

Immunohistologic Analyses

Immunohistology was performed on cryostat sections. Immunohistologic analysis for ENPP-1 was performed using a rabbit polyclonal antibody (Santa Cruz Biotechnology, Santa Cruz, Calif., USA). Slides were then incubated with EnVision® Dual Link System-HRP, followed by AEC substrate (Dako, Carpinteria, Calif., USA). Tissue sections were counterstained with hematoxylin. Rabbit serum was used as a negative control in all immunohistology experiments.

Determination of Valvular Calcium Concentrations

A segment of valve tissue was kept in liquid nitrogen until determination of the calcium content. Leaflets were cut in small pieces and treated with HCl 6N at 90° C. during 24 hours. Treated tissues were then centrifuged at 4400 RPM during 30 min and supernatants were collected. Calcium content was determined by the 0-cresolphtalein complexone method. Results were expressed as mg of calcium per wet weight of tissue (Ca mg/g ww).

Determination of Phosphodiesterase Activity

Phosphodiesterase activity was measured using the substrate p-nitrophenyl phenylphosphonate (PNPP-PP) (Sigma, Oakville, Ont, Canada). Proteins were isolated from normal control valves (n=14), AS valves (n=18) or valve interstitial cells (VICs) and used for enzyme activity. Cells were harvested with trypsine-EDTA (Invitrogen, Toronto, Ont, Canada), washed 2 times in washing buffer (NaCl 0.15M, TRIS-HCl pH 8.1, 20 mM, $CaCl_2$ 1 mM) and resuspended in assay buffer (NaCl 0.15M, TRIS-HCl pH 8.1, 20 mM, $CaCl_2$ 0.5 mM, 1 mM p-nitrophenyl phenylphosphonate). The same amount of proteins isolated from tissues were washed twice in washing buffer and resuspended in 600 μl of assay buffer. Then cells or tissue proteins were incubated at 37° C. until a yellow color developed and were then centrifuged for 5 min at 4° C., 450 G. The reaction was stopped by adding dithiothreitol to a final concentration of 10 mM. Absorbance was measured at 400 nm. Results were calculated using a molar absorption coefficient for p-nitrophenol of 18320 $M^{-1}$ $cm^{-1}$. The assay was carried out in triplicate. Results were normalized to protein content.

Valve Interstitial Cells Isolation and In Vitro Analyses of Calcification

Human valve interstitial cells (VICs) were isolated by collagenase digestion from explanted hearts during transplant procedures. Cells were cultured in DMEM containing 10% FBS, 2 mM L-glutamine and 1 mM sodium pyruvate (Invitrogen, Toronto, Ont, Canada). Cells were seeded in 12 well plates ($2 \times 10^4$ cells/well). To provoke calcification, cells were incubated with a pro-calcifying medium containing: DMEM+5% FBS, $10^{-7}$ M insulin, 50 μg/ml ascorbic acid and $NaH_2PO_4$ at 2 mM (in some experiments where it is specified $NaH_2PO_4$ was used at 1, 2 and 5 mM). VICs were cultured with or without calcification medium for 14 days. In some experiments ARL 67156 (a competitive inhibitor of ENPP-1) (10 μM and 25 μM) was added to the growth medium Studies were conducted at day 0, 7, 14 in triplicate. For calcium quantification, cells were decalcified with 0.6 M HCl for 24 h. The calcium content of the HCl supernatants was determined using the o-cresolphthalein complexone method. After decalcification, cells were washed with PBS and solubilised with 0.1 N NaOH/0.1% SDS. The protein content was determined using Biorad® assay kit (Biorad, Mississauga, Ont, Canada). Cells calcium content was normalized to protein content.

Immunoprecipitation and Western Blot

VICs were harvested in 200 mM Tris-HCl pH 6.8, 2% SDS+protease inhibitor (Roche diagnostic, Laval, QC, Can). The protein concentration of supernatant was determined with DC protein assay from Bio-Rad. For immunoprecipitation, cells were incubated with 20 μl of mouse polyclonal antibody directed against ENPP1 (Cedarlane, Hornby, Ont., Can.) at 4° C., 0/N on a rotating wheel. After 3 washes with PBS, 50 µl of protein G Sepharose™ beads (Sigma, Oakville, Ont., Canada) was added and the mixture was incubated again at 4° C. overnight on a rotating wheel. After three more washes, beads were resuspended in SDS-sample buffer and boiled at 95° C. For western analysis, proteins were loaded onto 6% SDS-polyacrylamide gels followed by electrophoresis and blotting onto nitrocellulose membranes. Membranes were blocked with TBS-tween containing 5% non-fat dry milk, incubated with mouse polyclonal antibody directed against ENPP1 followed by an HRP-labelled anti-mouse IgG antibody (Amersham, Piscataway, N.J., USA). Detection was done with Supersignal West Pico chemiluminescent substrate (Pierce Lab, Rockford, Ill., USA).

Animal Study

Animal experiments were approved by the Animal Care and Use Committee of Laval and Montreal Universities. Male Wistar rats (initial weight 200 g) were obtained from Charles River Breeding Laboratories (St Constant, Qc, Canada). The animals received warfarin (20 mg/kg/day in drinking water) and vitamin K (phylloquinone) (15 mg/kg/day subcutaneous injection) (WVK) (n=10) at day 1, 3, 5, 7, 14, 21, and 28. Dosages were adjusted every second day. Controls consisted of age-matched untreated rats (n=7). In two other groups of rats, ARL 67156 was administered at 0.55 µg/kg/day (n=10) and 1.1 µg/kg/day (n=10) during 28 days with osmotic pumps implanted subcutaneously. At day 28, animals were anesthetized with pentobarbital (65 mg/kg) for blood plasma sampling and the harvesting of aorta and heart. Segments of the aorta were frozen at −80° C. for the determination of calcium amount. The heart with the aortic root and valve was fixed in formaldehyde 10% for histological processing and immuno-histology. Transversal sections (5 µm) of the aortic root were stained with H&E and von Kossa (for calcium). Morphometric analyses of the aortic root (at the level of aortic valve and sinuses of Valsalva) were carried out using the Image-Pro Plus (MediaCybernetics, Bethesda, Md., USA) image analysis software to quantify the calcified areas (with the von Kossa staining) normalized to the total surface area of the section.

Statistical Analyses

For comparisons of the groups with regards to q-PCR analyses, enzyme activity, and the amount of valvular calcium, results were expressed as means ±SEM. For continuous data, values were compared between groups with Student t-test or ANOVA when two or more than two groups were compared, respectively. Post hoc Tukey analyses were done when the p value of the ANOVA was <0.05. Correlations between variables were determined using Spearman's coefficients. Multiple linear regression analysis was used to identify the factors that are independently associated with the amount of ENPP-1 in AS valves. Variables with a p value ≦0.1 were entered in the multivariate models. A p value <0.05 was considered as statistically significant. Statistical analysis was performed with a commercially available software package JMP IN 5.1.

Example 2

Expression of Ectonucleotidases in Aortic Valves

A tissue-based microarray experiment was first conducted to explore the gene expression pattern of different ectonucleotidases on human aortic valves explanted from patients with or without AS. Five calcified AS valves and 5 control valves without any signs of calcification or dysfunction were selected for the microarray experiment. Cases and controls were Caucasian males without renal failure, matched for age and body mass index. Only tricuspid valves were used. Two control valves failed quality control and were discarded from subsequent analyses. The microarray results for key enzymes regulating the Pi/PPi ratio are presented in FIG. 1. The heat map illustrates the normalized expression values for each sample. A total of 21 probe sets were available to study the expression of 7 relevant enzymes: ENPP (1-2-3), ENTPD (1-2-3), and NT5E. The ENPP1 mRNA transcript was increased by 3.9-fold in AS compared to control valves. None of the other enzymes were significantly regulated in the microarray dataset. Results of the microarray were validated by quantitative PCR analyses in a larger cohort of 87 AS valves and in 14 non-calcified control valves. Within the population with AS there were 34 females (39%) and the proportion of bicuspid valves was 25% (n=22). Quantitative PCR analyses confirmed the results of the microarray experiment with 3.7-fold more copies of ENPP-1 in AS valves compared to control valves (p=0.007) (FIG. 2A).

Figure 2:
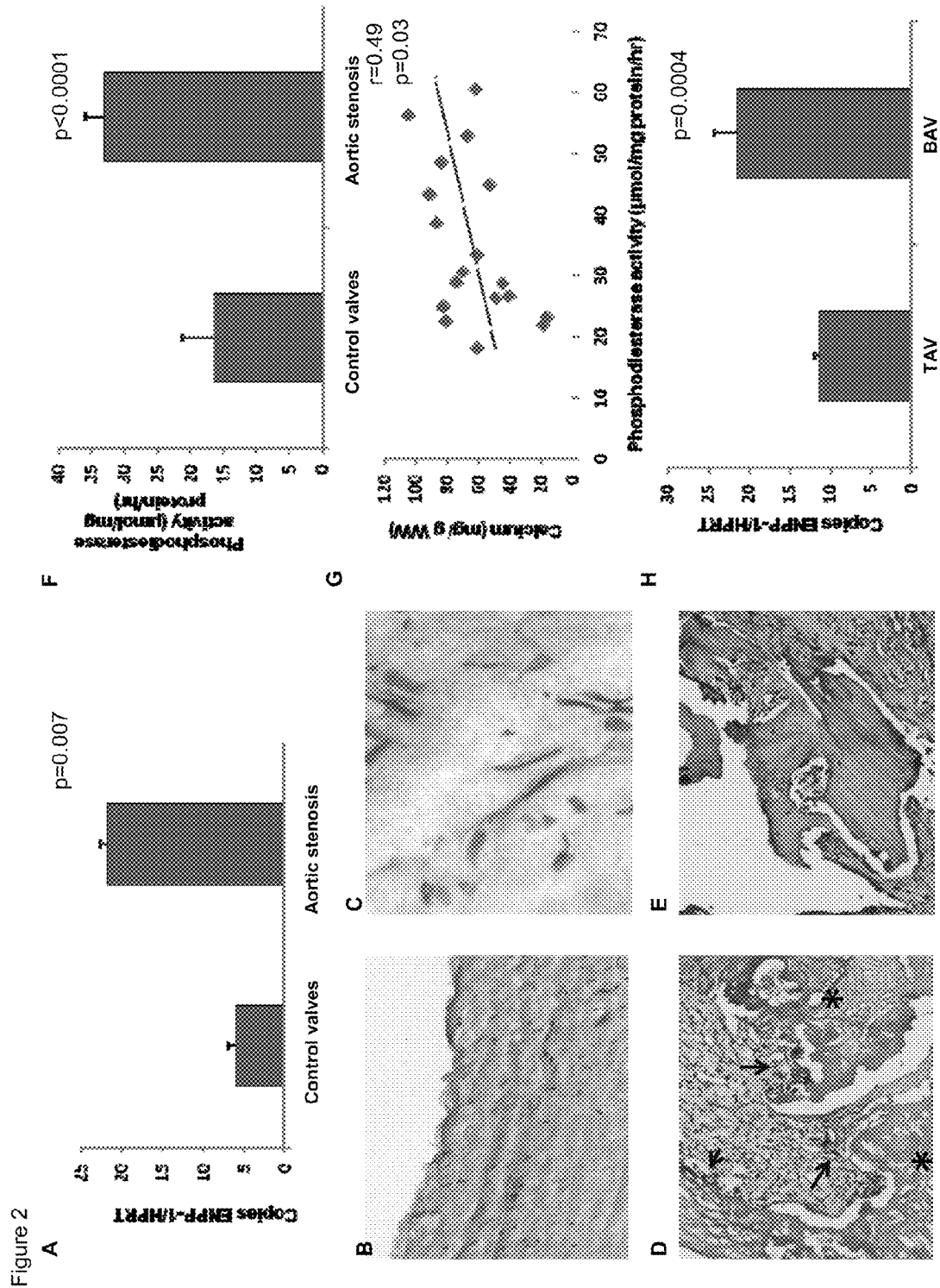
FIG. 2: Expression and enzymatic activity of ENPP-1 in normal and aortic stenotic valves (A to F). (A) Quantitative-PCR showed a higher number of copies of ENPP-1 in aortic stenosis compared to control valves. (B) Immunohistochemistry studies demonstrated that normal control valves had a basal level of ENPP-1 expression (200 X), (C) which was localized to valve interstitial cells (1000 X). (D) In aortic stenosis valves, ENPP-1 was strongly expressed (arrows) at the periphery of calcified areas (marked with an *) (200 X). (E) In some patients with aortic stenosis, lamellar bone-like tissue was present along with ENPP-1 expression (200 X). (F) Increased enzymatic ENPP activity measured with phosphodiesterase assay was also documented in aortic stenotic valves compared to control valves. (G) Phosphodiesterase activity was positively and significantly related to the amount of calcium measured into aortic stenosis valves (r=0.49; p=0.03). (H) Bicuspid aortic valves (BAV) had significantly more copies of ENPP-1 when compared to tricuspid aortic valves (TAV)

Using immunohistology, we documented the presence of ENPP-1 in control valves (FIG. 2B). The staining was dispersed in valve interstitial cells (VICs), which are fibroblast cells of the valve matrix (FIG. 2C). In AS valves, we found a stronger immunoreactivity for ENPP-1, which was localized at the periphery and within the calcified areas, suggesting an implication of this enzyme in the calcifying process (FIG. 2D). In some patients, mature lamellar bone-like tissue was observed and colocalized with enhanced expression of ENPP-1 (FIG. 2E). In order to have a functional assessment of ENPP-1, phosphodiesterase activity was measured in control and AS valves. Using this assay we found a significantly elevated phosphodiesterase activity in AS valves when compared to control tissues (p<0.0001) (FIG. 2F). To further assess the relationship between ENPP activity and mineralization process, we documented the amount of calcium in 18 valves along with phosphodiesterase activity. We found that phosphodiesterase activity was significantly and positively associated with the level of calcium measured in AS valves (r=0.49; p=0.03) (FIG. 2G).

Example 3

Clinical Factors Associated with ENPP-1 Expression in Aortic Stenosis Valves

Among the different clinical factors, we found that bicuspid valves had markedly higher level of ENPP-1 copies when compared to tricuspid valves (p=0.0004) (FIG. 2H). In addition, we documented a significant and positive correlation between the diastolic blood pressure and the number of ENPP-1 copies (r=0.34; p=0.001) (data not shown). Among the other factors, we have also documented that the number of ENPP-1 copies were significantly lower in patient taking angiotensin receptor blockers (ARBs) medication (p=0.04) (data not shown). However, patients under angiotensin converting enzyme inhibitors (ACE inhibitors) treatment had similar number of ENPP-1 copies compared to subjects not taking this medication. On linear multivariate regression model, after adjustment for age, gender, and ARBs medication, we found that only diastolic blood pressure (p=0.02) and bicuspid valves (p=0.03) were independently related to the amount of ENPP-1 (determined by quantitative-PCR) in AS valves ($r^2$ adjusted=0.24; p<0.0001) (data not shown). Noteworthy, the number of ENPP-1 copies in AS valves was directly related to peak transvalvular pressure gradient measured by Doppler-echocardiography prior to aortic valve replacement surgery (r=0.31; p=0.006), and with the annualized progression rate of gradient during the years preceding surgery (r=0.37; p=0.02).

Role of ENPP-1 in Isolated Valve Interstitial Cells from Aortic Valves

Figure 3:
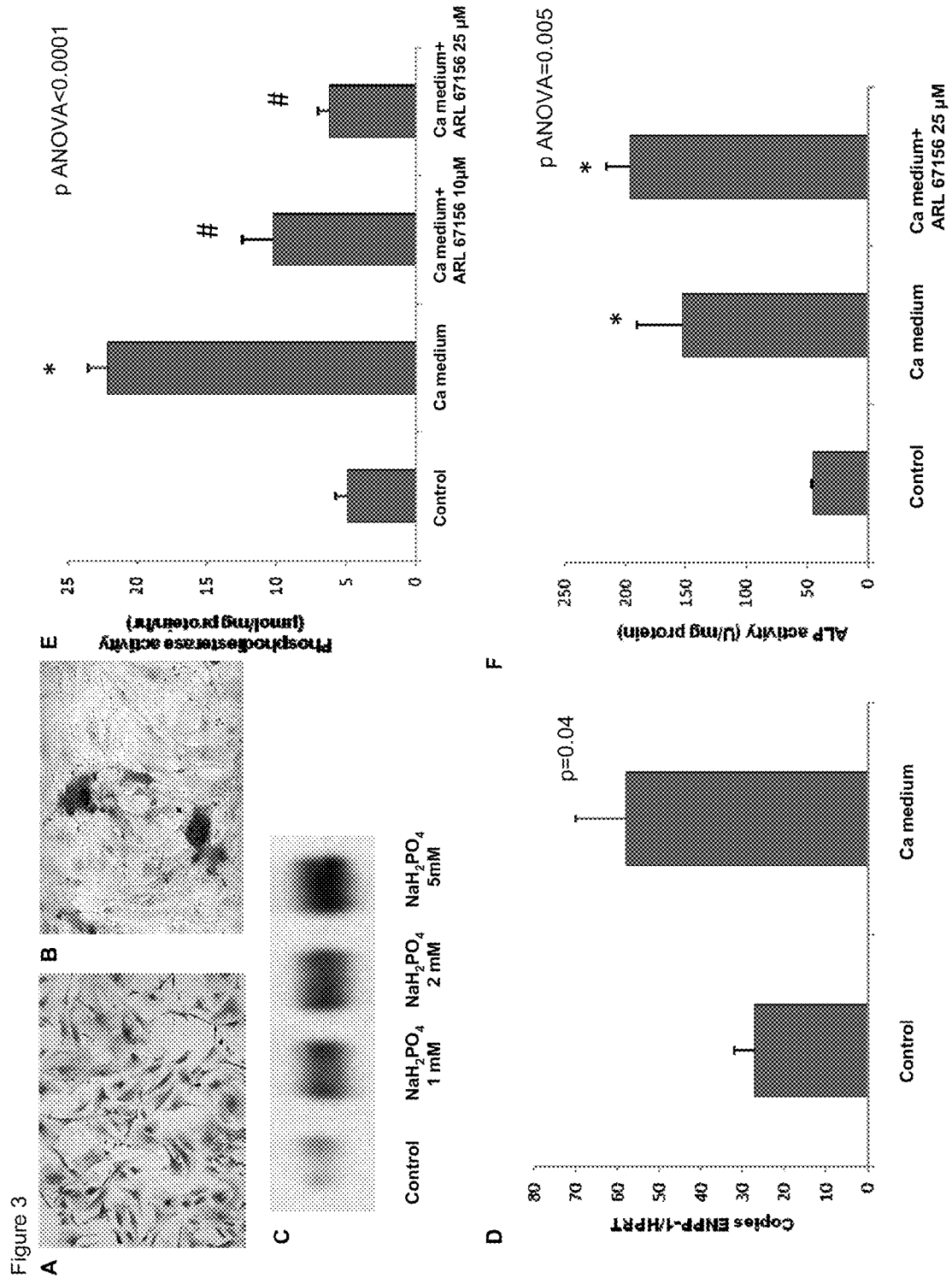
FIG. 3: Expression and enzymatic activity of ENPP-1 in vitro (A to E). (A) Valve interstitial cells (VICs) had a basal level of expression of ENPP-1 as shown by immunohistochemistry; (B) upon exposition to the calcifying medium for 14 days, VICs formed calcified nodules as shown with alizarin red staining (appearing in dark); (C) at day 14 the expression of ENPP-1 at the protein level was dose-dependently increased by different concentrations of $NaH_2PO_4$ (immunoprecipitation); (D) quantitative-PCR analyses confirmed that after 14 days of treatment with the calcifying medium (Ca medium) ($NaH_2PO_4$ 2 mM), VICs had a higher number of copies of ENPP-1. (E) Over 14 days of treatment with the calcifying medium, VICs increased their phosphodiesterase activity, which was dose-dependently decreased by ARL 67156 (10 µM and 25 µM), a competitive inhibitor of ENPP-1. (F) The effect of ARL 67156 was specific to phosphodiesterase and did not affect the alkaline phosphatase activity, which was increased by treatment with the calcifying medium (Ca medium). *$p<0.05$ compared to control; #$p<0.05$ compared to calcifying medium.
Figure 4:
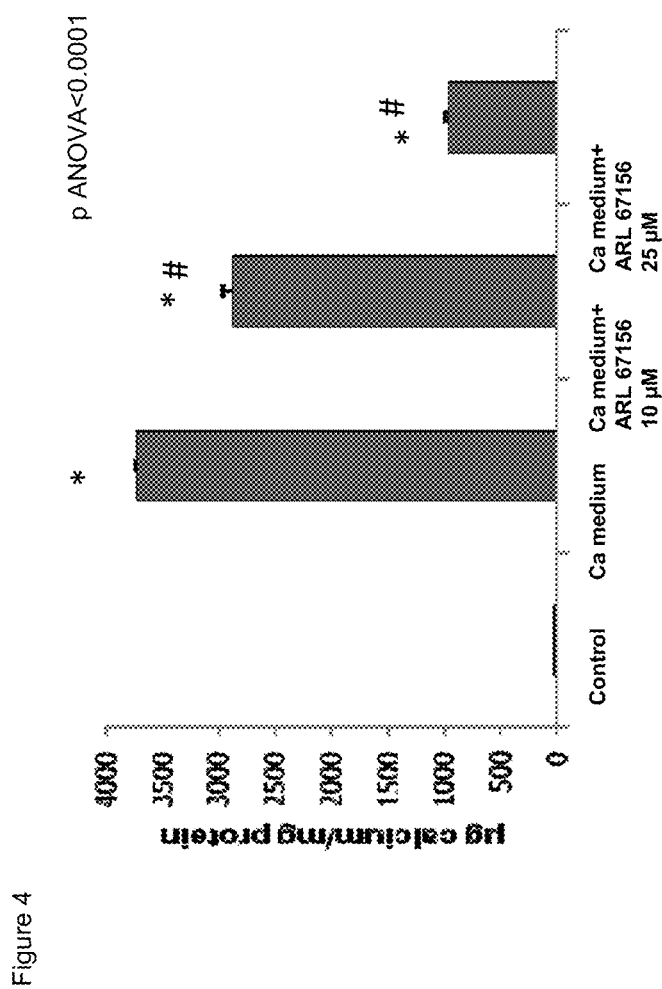
FIG. 4: Effect of ARL 67156 on the calcification of valve interstitial cells.

In isolated human VICs from non-calcified control valves studied by immunohistology, we found that ENPP-1 was expressed by all cells (FIG. 3A). After exposition of VICs to a calcifying medium (NaH$_2$PO$_4$) for 14 days, cells formed calcified nodules as demonstrated with the alizarin red staining (FIG. 3B). Of particular interest, exposition of cells for 14 days with different concentrations of NaH$_2$PO$_4$ led to a dose-dependent increase of ENPP-1 at the protein level (FIG. 3C). Increased copies of mRNA of ENPP-1 upon stimulation with 2 mM of NaH$_2$PO$_4$ was also confirmed with quantitative PCR analyses (p=0.04) (FIG. 3D). Phosphodiesterase activity in isolated VICs also increased significantly at day 14 after treatment with the calcifying medium (FIG. 3E). To further gain insight into the role of ENPP activity on the calcifying process of the aortic valve we used a competitive inhibitor, ARL 67156 (5). Incubation of VICs with ARL 67156 significantly reduced phosphodiesterase activity after exposition to the calcifying medium (FIG. 3E). To confirm that ARL 67156 provides specific inhibition on phosphodiesterase activity, the level of alkaline phosphatase (ALP) activity was also measured. After exposition of cells to the calcifying medium, ALP activity increased significantly and was not affected by ARL 67156 (FIG. 3F). Of particular significance, ARL 67156 dose-dependently reduced the calcification of isolated VICs at day 14 after treatment with the calcifying medium (p<0.0001) (FIG. 4).

Example 4

Effect of Ectonucleotidase Inhibition in vivo

Figure 5:
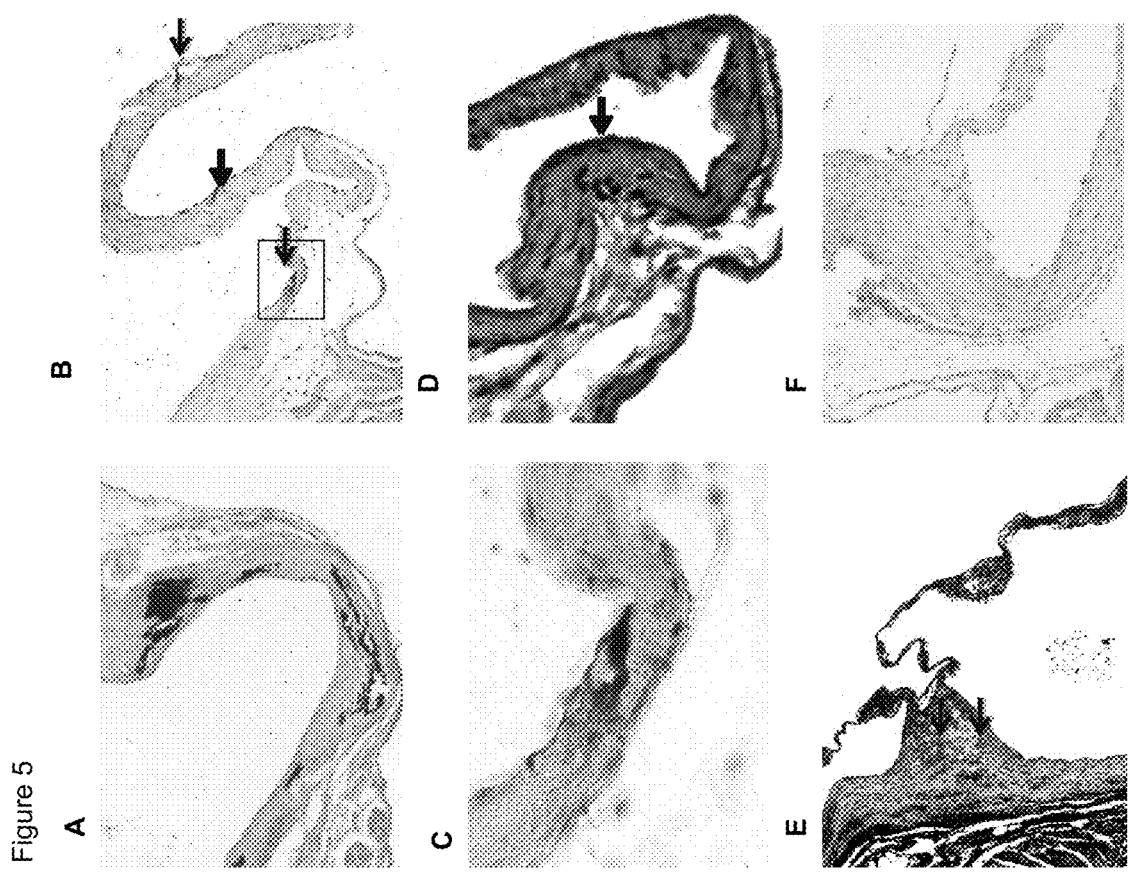
FIG. 5: Calcification and expression of ENPP-1 in rats treated with warfarin in presence or absence of ARL 67156 treatment (A to F). (A) In rats treated with warfarin, calcifications developed in the aortic root (von Kossa) (calcification appears in black); (B) in animals treated with warfarin early foci of calcifications were detected on the aortic cusps (200 X) (arrows); (C) higher magnification of area in square in panel (B) is shown (400 X); (D) ENPP-1 was only detected with immunostaining (arrows) in mineralized areas of cusps (area in square in panel B) (400 X) and (E) aortic root (200 X); in panel (F) an aortic root at the level of aortic cusp is shown without calcification in a rat treated with ARL 67156 (1.1 µg/kg/d) (200 X).

We next investigated whether the inhibition of ENPP activity may also prevent aortic calcification in vivo. Aortic calcifications can be induced in rats by the administration of warfarin and vitamin K (the latter being given to reduce the incidence of bleeding) (WVK). Warfarin is a potent inhibitor of the γ-carboxylation of matrix gla-protein (MGP), which is a key molecule preventing ectopic calcification. In rats treated for 28 days with WVK regimen, we observed important calcifications of the aorta and aortic root (FIG. 5A). In animals treated with WVK we also observed foci of calcification within the aortic valve cusps (FIG. 5, B and C). Immunostaining of sections at the level of the aortic root revealed that ENPP-1 was expressed only in calcified areas (FIG. 5, D and E) and was not observed in control animals. Calcification of the valve cusps was not detected in the two groups of rats treated with ARL 67156 (doses of 0.55 μg/kg/d and 1.1 μg/kg/d delivered with an osmotic pump) (FIG. 5F).

Conclusion

This is the first study to demonstrate that ENPP-1 is highly expressed in AS valves and is a key regulator of the calcifying process. The markedly elevated level of ENPP-1 expression in bicuspid aortic valves may explain the early onset of mineralization and the high magnitude of calcification of valvular tissue observed in patients with this congenital abnormality. Given that no medical treatment is yet available for the prevention or treatment of AS and that the only option currently available for the treatment of severe AS is valve replacement surgery, this study may open novel and promising avenues for the development of a new class of drugs, ectonucleotidase inhibitors, which may eventually prove successful to prevent the progression of this frequent and serious cardiovascular disease.

Reference List

1. Giachelli, C. M., Jono, S., Shioi, A., Nishizawa, Y., Mori, K., and Morii, H. 2001. Vascular calcification and inorganic phosphate. *Am. J. Kidney Dis.* 38:S34-S37.
2. Rutsch, F., Vaingankar, S., Johnson, K., Goldfine, I., Maddux, B., Schauerte, P., Kalhoff, H., Sano, K., Boisvert, W. A., Superti-Furga, A. et al 2001. PC-1 nucleoside triphosphate pyrophosphohydrolase deficiency in idiopathic infantile arterial calcification. *Am. J. Pathol.* 158:543-554.
3. Masuda, I., and Hirose, J. 2002. Animal models of pathologic calcification. *Curr. Opin. Rheumatol.* 14:287-291.
4. Johnson, K., Hashimoto, S., Lotz, M., Pritzker, K., Goding, J., and Terkeltaub, R. 2001. Up-regulated expression of the phosphodiesterase nucleotide pyrophosphatase family member PC-1 is a marker and pathogenic factor for knee meniscal cartilage matrix calcification. *Arthritis Rheum.* 44:1071-1081.
5. Levesque, S. A., Lavoie, E. G., Lecka, J., Bigonnesse, F., and Sevigny, J. 2007. Specificity of the ecto-ATPase inhibitor ARL 67156 on human and mouse ectonucleotidases. *Br. J. Pharmacol.* 152:141-150.
6. Thouverey, C., Bechkoff, G., Pikula, S., and Buchet, R. 2009. Inorganic pyrophosphate as a regulator of hydroxyapatite or calcium pyrophosphate dihydrate mineral deposition by matrix vesicles. *Osteoarthritis. Cartilage.* 17:64-72.

The invention claimed is:

1. A method for identifying a potential inhibitor of aortic valve stenosis or cardiovascular calcification, comprising the steps of:
    a) contacting ectonucleotidase pyrophosphate/phosphodiesterase-1 (ENPP-1) with a potential inhibitor compound thereof; and
    b) measuring the level of ENPP-1 activity in contact with said inhibitor as per step a);
    c) measuring the level of ENPP-1 activity in absence of inhibitor to define a control activity;
    d) comparing said activity from step b) with control activity from step c);
    e) selecting a compound that yields ENPP-1 activity from step b) that is lower than control ENPP-1 activity, wherein a lower activity of ENPP-1 is an indication that said compound is a potential inhibitor of aortic valve stenosis or cardiovascular calcification; and
    f) further testing said compound from step e) for a decrease in calcification in an in vitro model of cellular mineralization.

2. The method of claim 1, wherein the level of ENPP-1 activity is measured by way of measuring the production of Pi, whereby a decreased production of Pi is an indication that the ENPP-1 activity is decreased.

3. The method of claim 1, wherein the level of ENPP-1 activity is measured by way of measuring the production of PPi, whereby decreased production of PPi is an indication that the ENPP-1 activity is decreased.

4. The method of claim 1, wherein said ENPP-1 activity is measured using p-nitrophenyl phenylphosphonate (PNPP-PP) as a substrate and the reaction is followed by measuring absorbance of resulting p-nitrophenol at 400 nm.

5. The method according to claim 1 or 4, further comprising the step:
    g) further testing said compound from step e) or f) for a decrease or delay in calcification of aortic valve in a mammal.

6. The method of claim 5, wherein said mammal is rodent or human.

7. The method of claim 1 or 4, wherein said in vitro model of cellular mineralization comprises isolated valve interstitial cells.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: PCR Primer

<400> SEQUENCE: 1
tgcccctttg gacatcctat acc                23

<210> SEQ ID NO 2
<211> LENGTH: 20
<212> TYPE: DNA
<213> ORGANISM: Artificial Sequence
<220> FEATURE:

```
<223> OTHER INFORMATION: PCR Primer

<400> SEQUENCE: 2
ttgtggtggg gagaggaacc                                           20

<210> SEQ ID NO 3
<211> LENGTH: 20
<212> TYPE: DNA
<213> ORGANISM: Artificial Sequence
<220> FEATURE:
<223> OTHER INFORMATION: PCR Primer

<400> SEQUENCE: 3
tggcgtcgtg attagtgatg                                           20

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
aatccagcag gtcagcaaag                                           20
```